(12) United States Patent
Shi et al.

(10) Patent No.: US 7,502,445 B2
(45) Date of Patent: Mar. 10, 2009

(54) RADIOGRAPHING PLAN ASSISTING METHOD AND X-RAY CT SYSTEM

(75) Inventors: Yilun Shi, Beijing (CN); Xueli Wang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 73 days.

(21) Appl. No.: 11/531,929

(22) Filed: Sep. 14, 2006

(65) Prior Publication Data
US 2007/0211844 A1 Sep. 13, 2007

(30) Foreign Application Priority Data
Sep. 15, 2005 (CN) .................. 2005 1 0109918

(51) Int. Cl.
*G01N 23/083* (2006.01)
(52) U.S. Cl. .................. 378/115; 378/62; 378/95
(58) Field of Classification Search .................. 378/62, 378/95, 115
See application file for complete search history.

(56) References Cited

U.S. PATENT DOCUMENTS

| | | | | |
|---|---|---|---|---|
| 3,916,192 A | * | 10/1975 | Schmitmann et al. | ......... 378/98 |
| 4,080,536 A | * | 3/1978 | Brehm et al. | .................. 378/92 |
| 4,160,906 A | * | 7/1979 | Daniels et al. | ................. 378/97 |
| 4,247,777 A | * | 1/1981 | Pfeifer et al. | .................. 378/98 |
| 4,255,662 A | * | 3/1981 | Waterkamp | ................. 378/116 |
| 4,773,086 A | * | 9/1988 | Fujita et al. | ..................... 378/4 |
| 4,816,680 A | * | 3/1989 | Nakajima et al. | ........... 250/590 |
| 5,986,662 A | | 11/1999 | Argiro et al. | |
| 6,272,469 B1 | | 8/2001 | Koritzinsky et al. | |
| 6,633,627 B2 | * | 10/2003 | Horiuchi | ..................... 378/156 |
| 6,795,528 B2 | * | 9/2004 | Nokita | ........................ 378/155 |
| 6,901,371 B1 | | 5/2005 | Koritzinsky et al. | |
| 6,944,269 B2 | * | 9/2005 | Schmitt | ....................... 378/115 |
| 6,988,074 B2 | | 1/2006 | Koritzinsky et al. | |
| 7,031,423 B2 | * | 4/2006 | Tsukagoshi | .................... 378/4 |

FOREIGN PATENT DOCUMENTS

JP        2002-085395        3/2002

* cited by examiner

*Primary Examiner*—Edward J Glick
*Assistant Examiner*—Thomas R Artman
(74) *Attorney, Agent, or Firm*—Armstrong Teasdale LLP

(57) ABSTRACT

With a view to providing a radiographing plan assisting method which can easily prepare a radiographing plan by utilizing a user interface, it is made possible to select an anatomical region through a user interface, select through a user interface an anatomical area belonging to the selected anatomical region, select a radiographing protocol for the selected anatomical area through a user interface, and select a feature of the selected radiographing protocol through a user interface.

14 Claims, 8 Drawing Sheets

Feature Name = {V00, V10, V20, V30, V40, V50, V60, V70, V80, V90}\
              {V01, V11, V21, V31, V41, V51, V61, V71, V81, V91}\
              {V02, V12, V22, V32, V42, V52, V62, V72, V82, V92}\
              {V03, V13, V23, V33, V43, V53, V63, V73, V83, V93}\
              {V04, V14, V24, V34, V44, V54, V64, V74, V84, V94}\

Fig. 10

ECG Trace = {V00=F,V10=F,V20=F,V30=F,V40=T,V50=F,V60=F,V70=F,V80=F,V90=F}\
          {V01=F,V11=F,V21=F,V31=F,V41=T,V51=F,V61=F,V71=F,V81=F,V91=F}\
          {V02=F,V12=F,V22=F,V32=F,V42=T,V52=F,V62=F,V72=F,V82=F,V92=F}\
          {V03=F,V13=F,V23=F,V33=F,V43=T,V53=F,V63=F,V73=F,V83=F,V93=F}\
          {V04=F,V14=F,V24=F,V34=F,V44=T,V54=F,V64=F,V74=F,V84=F,V94=F}\

RADIOGRAPHING PLAN ASSISTING METHOD AND X-RAY CT SYSTEM

CROSS REFERENCE TO RELATED APPLICATIONS

This application claims the benefit of Chinese Application No. 200510109918.0 filed Sep. 15, 2005.

BACKGROUND OF THE INVENTION

The present invention relates to a radiographing plan assisting method and an X-ray CT (computed tomography) system. Particularly, the present invention is concerned with a radiographing plan assisting method which utilizes a user interface, as well as an X-ray CT system having a user interface for assisting a radiographing plan.

The X-ray CT system is adapted to collect transmitted X-ray signals of plural views of a subject with use of an X-ray irradiator/detector which is rotating within a gantry and reconstruct a tomographic image on the basis of the transmitted X-ray signals. The rotation of the X-ray irradiator/detector is also called scan. The transmitted X-ray signals thus collected are also called scan data.

The X-ray CT system has a user interface. The user interface comprises a graphical user interface, through which a user can operate the X-ray CT system interactively. The user interface is used also for preparing a scan plan (see, for example, Patent Literature 1).

[Patent Literature 1]Japanese Unexamined Patent Publication No. 2002-85395 (pp. 5-6, FIGS. 4-6)

The preparation of a scan plan is performed by selecting a radiographing protocol best suited for an anatomical site from among plural radiographing protocols stored beforehand in the X-ray CT system. With diversification of radiographing protocols, the operation of a user interface for preparing a scan plan is becoming more and more complicated. Consequently, it takes times to prepare a scan plan and as the case may be the user is perplexed.

SUMMARY OF THE INVENTION

Therefore, it is an object of the present invention to provide a radiographing plan assisting method which can prepare a radiographing plan easily by utilizing a user interface and an X-ray CT system having a user interface easy to prepare a radiographing plan.

In one aspect of the present invention for solving the above-mentioned problem there is provided a radiographing plan assisting method comprising enabling selection of a anatomical region through a user interface, enabling selection of an anatomical area belonging to the selected anatomical region through a user interface, enabling selection of a radiographing protocol for the selected anatomical area through a user interface, and enabling selection of a feature of the selected radiographing protocol through a user interface.

In another aspect of the present invention for solving the above-mentioned problem there is provided an X-ray CT system wherein a tomographic image is reconstructed on the basis of scan data obtained by scanning a subject with X-ray, the X-ray CT system comprising a user interface enabling selection of an anatomical region, a user interface enabling selection of an anatomical area belonging to the selected anatomical region, a user interface enabling selection of a radiographing protocol for the selected anatomical area, and a user interface enabling selection of a feature of the selected radiographing protocol.

In point of optimizing for each user it is preferable that the user interface enabling selection of the anatomical area include a user interface capable of being customized by a user.

In point of optimizing for each user it is preferable that the user interface enabling selection of the anatomical protocol include a user interface capable of being customized by a user.

In point of facilitating management by the system it is preferable that the feature have a configuration file.

In point of facilitating preparation of the configuration file it is preferable that the configuration file be a matrix with columns or rows corresponding to anatomical regions and rows or columns corresponding to anatomical areas.

According to the above aspects of the present invention it is made possible to select an anatomical region through a user interface, select an anatomical area belonging to the selected anatomical region through a user interface, select a radiographing protocol for the selected anatomical area through a user interface and select a feature of the selected radiographing protocol through a user interface. Therefore, it is possible to provide a radiographing plan assisting method which can prepare an anatomical plan easily by utilizing a user interface, as well as an X-ray CT system having a user interface easy to prepare a radiographing plan.

Further objects and advantages of the present invention will be apparent from the following description of the preferred embodiments of the invention as illustrated in the accompanying drawings.

BRIEF DESCRIPTION OF THE DRAWINGS

FIG. 7 illustrates, using a half-tone photograph, a user interface displayed on a display;

FIG. 9 illustrates a configuration file of a feature; and

FIG. 10 also illustrates a configuration file of a feature.

DETAILED DESCRIPTION OF THE INVENTION

Figure 1:
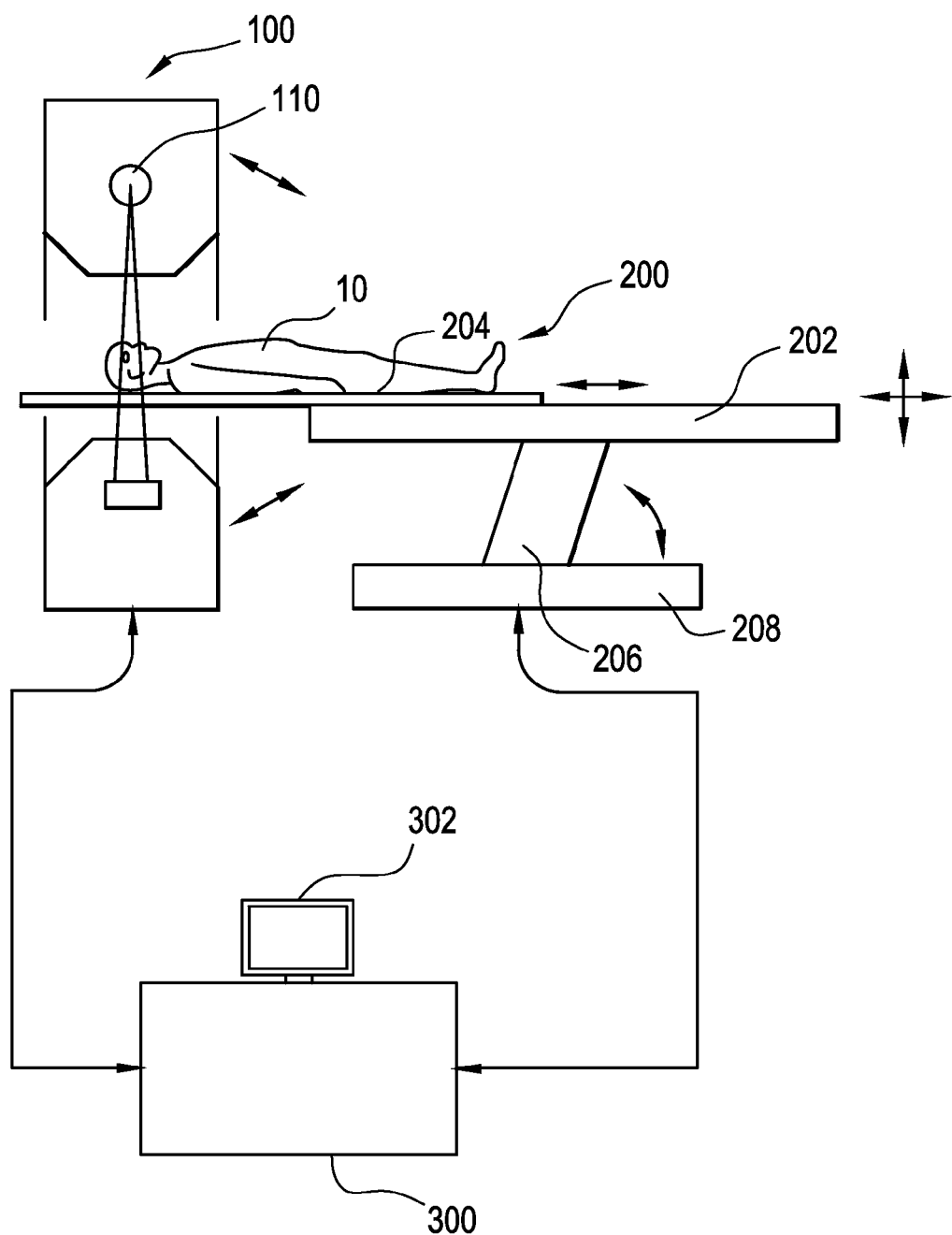
FIG. 1 illustrates the construction of an X-ray CT system according to an example of the best mode for carrying out the present invention.

The best mode for carrying out the present invention will be described hereinunder with reference to the drawings. The present invention is not limited to the best mode for carrying out the invention. A schematic configuration of an X-ray CT system is shown in FIG. 1. This system is an example of the best mode for carrying out the present invention. By the configuration of this system there is shown an example of the best mode for carrying out the invention related to an X-ray CT system. By the operation of this system there is shown an example of the best mode for carrying out the invention related to a radiographing plan assisting method.

The illustrated system has a gantry 100, a table 200 and an operator console 300. In the gantry 100, a subject 10 which is carried in by the table 200 is scanned by an X-ray irradiator/detector 110 and transmitted X-ray signals (scan data) of plural views are collected and inputted to the operator console 300. On the basis of the scan data inputted from the gantry 100 the operator console 300 performs image reconstruction and displays the reconstructed image on a display 302.

The operator console 300 also displays on the display 302 a user interface for enabling a user to operate the system interactively. A user interface for assisting a radiographing plan to be described later is included in the user interface. The display for the user interface may be separate from the display for the reconstructed image.

The operator console 300 controls the operation of the gantry 100 and that of the table 200. Under the control by the operator console 300, the gantry 100 performs scanning under predetermined scan conditions and effect positioning of the subject 10 so that a predetermined site of the table 200 is scanned. The positioning is performed by adjusting the height of a top board 202 and the distance of a horizontal movement of a cradle 204 mounted on the top board. Adjustment is performed using a built-in position adjusting mechanism.

By performing scan in a standstill state of the cradle 204 it is possible to effect an axial scan. A helical scan can be effected by performing scan plural times continuously under continuous movement of the cradle 204. Further, it is possible to effect a cluster scan by performing scan at every stop position under intermittent movement of the cradle 204.

The height of the top board 202 is adjusted by a swing motion of a support rod 206 centered on a mounting potion thereof for mounting to a base 208. With a swing motion of the support rod 206, the top board 202 is displaced in both vertical and horizontal directions. The cradle 204 moves horizontally on the top board 202 to offset the horizontal displacement of the top board 202. In a certain particular scan condition, scan is performed in a tilted state of the gantry 100. Tilting of the gantry 100 is effected by a built-in tilting mechanism.

Figure 2:
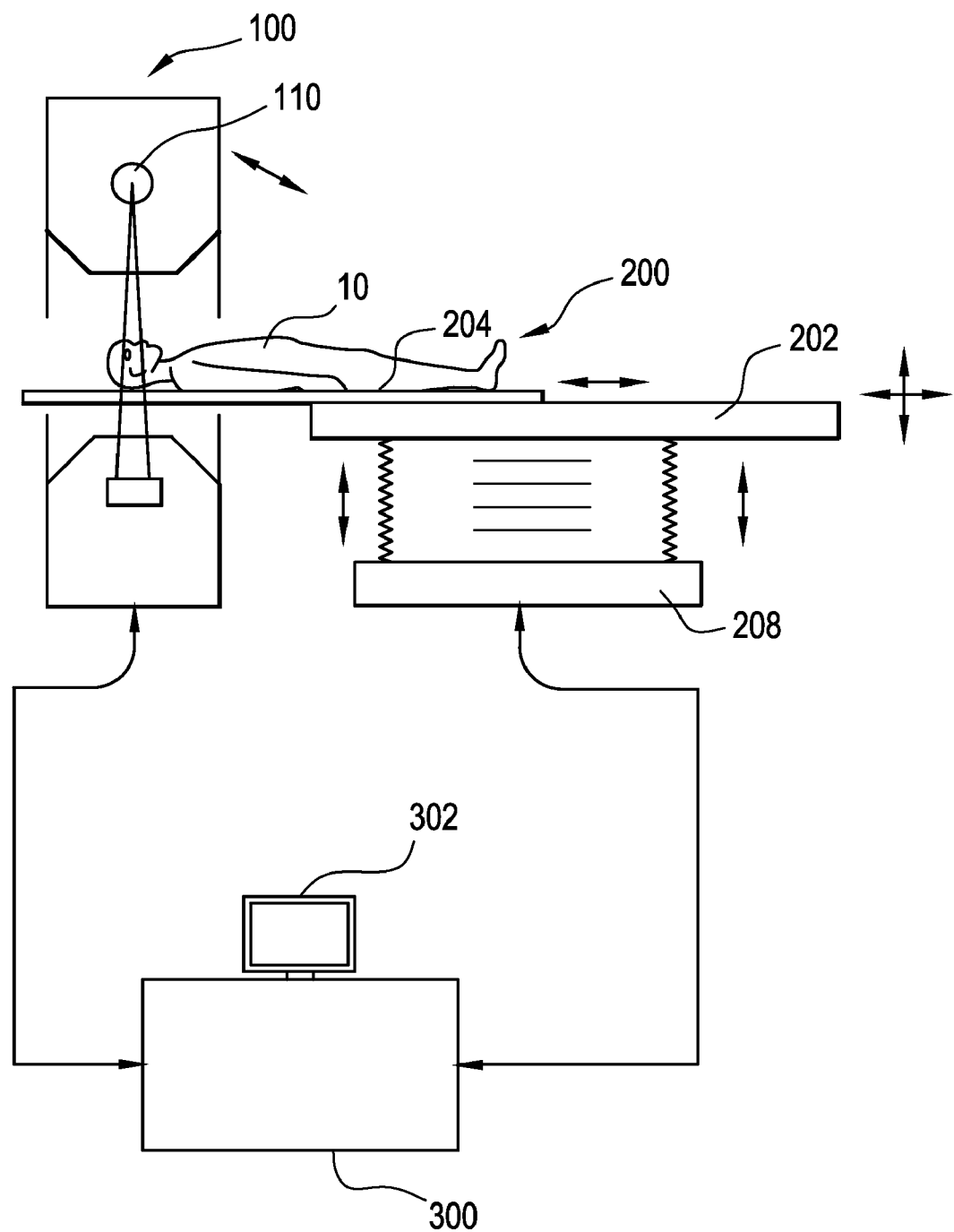
FIG. 2 illustrates the construction of an X-ray CT system according to another example of the best mode for carrying out the present invention.

As shown in FIG. 2, the table 200 may be of the type wherein the top board 202 moves up and down vertically with respect to the base 208. The vertical movement of the top board 202 is performed by a built-in lift mechanism. In the table 200, a horizontal movement of the top board 202 does not occur even under a vertical movement thereof.

Figure 3:
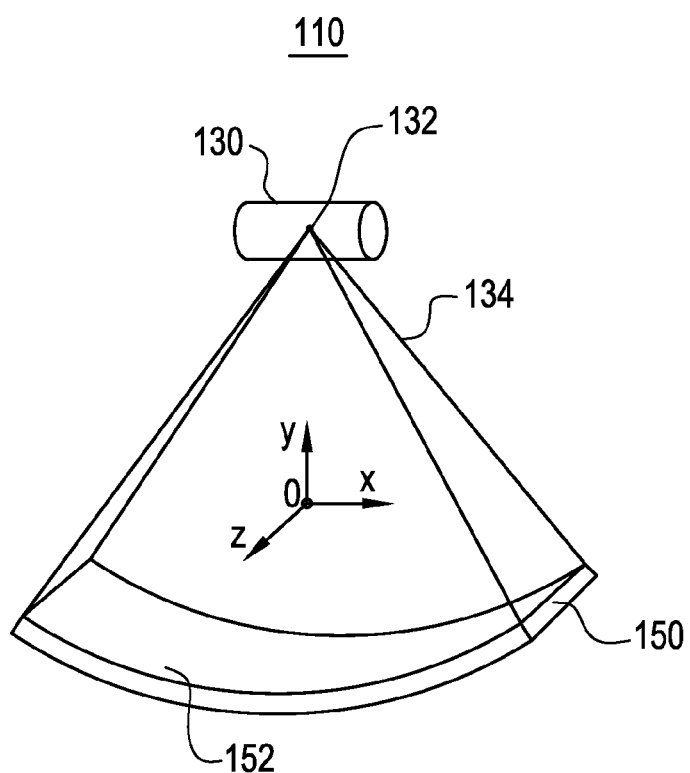
FIG. 3 illustrates the construction of an X-ray irradiator/detector.

The construction of the X-ray irradiator/detector 110 is shown schematically in FIG. 3. In the X-ray irradiator/detector 110, X-ray 134 radiated from a focal point 132 of an X-ray tube 130 is detected by an X-ray detector 150.

The X-ray 134 is shaped into a cone beam or fan beam symmetric right and left by means of a collimator (not shown). The X-ray detector 150 has an X-ray incidence plane 152 which spreads in two dimensions correspondingly to the spread of X-ray. The X-ray incidence plane 152 is curved so as to constitute a part of a cylinder. The axis of the cylinder passes through the focal point 132.

The X-ray irradiator/detector 110 rotates around an axis passing through a radiographic center, i.e., isocenter. The said axis is parallel to the axis of a partial cylinder formed by the X-ray detector 150.

It is assumed that a rotational axis direction is z direction, the direction joining the isocenter O and the focal point 132 is y direction, and the direction perpendicular to both z and y directions is x direction. The x, y and z directions constitute three axes in a rotational coordinate system with z axis serving as a center.

Figure 4:
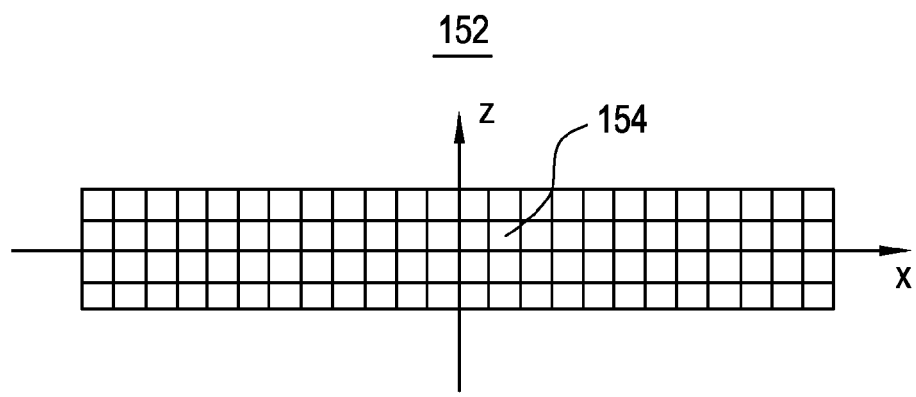
FIG. 4 illustrates the construction of an X-ray incidence plane in an X-ray detector.

FIG. 4 is a schematic plan view of the X-ray incidence plane 152 of the X-ray detector 150. Detection cells 154 are arranged two-dimensionally in both x and z directions. That is, the X-ray incidence plane 152 is a two-dimensional array of the detection cells 154. In case of using a fan beam of X-ray, the X-ray incidence plane 152 may be a one-dimensional array of the detection cells 154.

Each detection cell 154 constitutes a detection channel in the X-ray detector 150. Thus, the X-ray detector 150 is a multi-channel X-ray detector. For example, each detection cell 154 is constituted by a combination of a scintillator and a photo diode.

Figure 5:
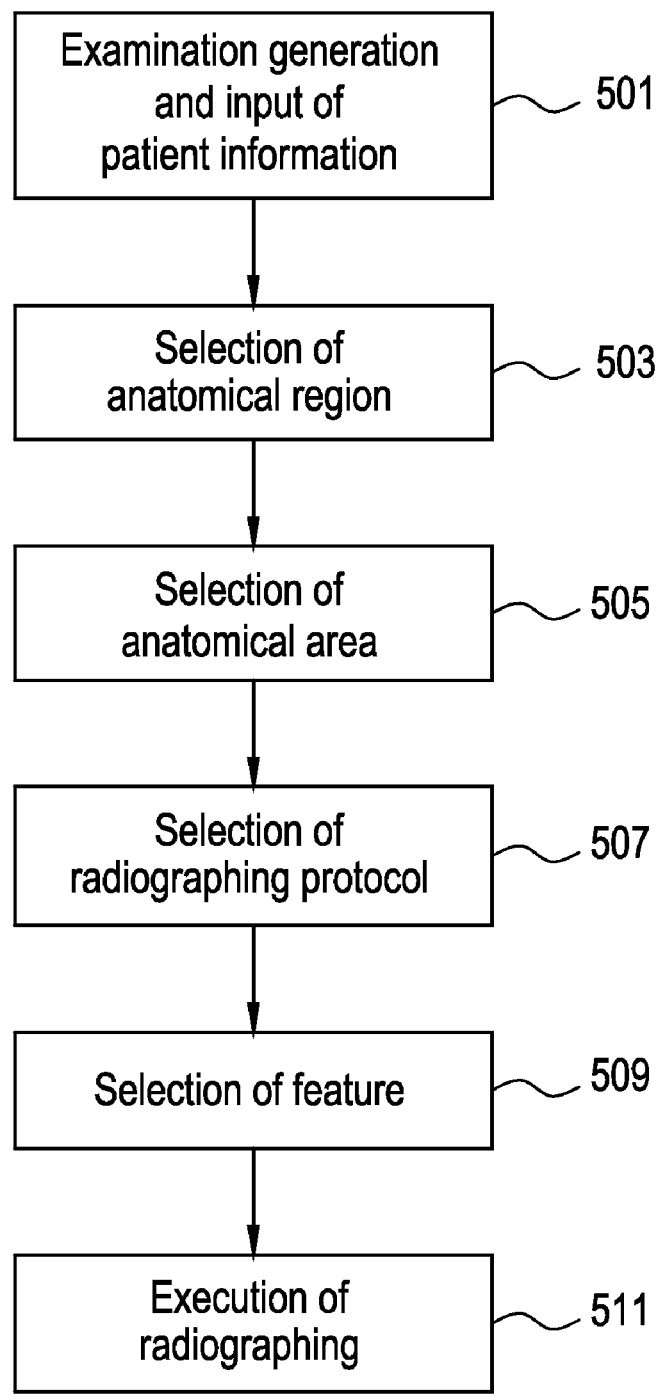
FIG. 5 illustrates a work flow for preparing a radiographing plan.
Figure 6:
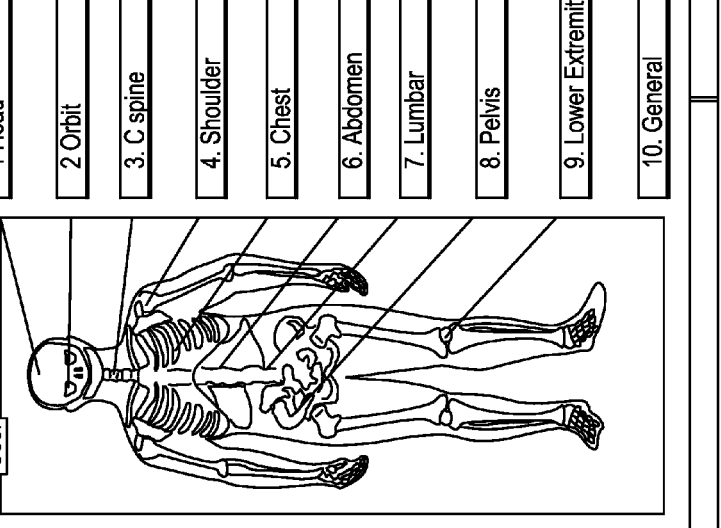
FIG. 6 illustrates, using a half-tone photograph, a user interface displayed on a display.
Figure 7:
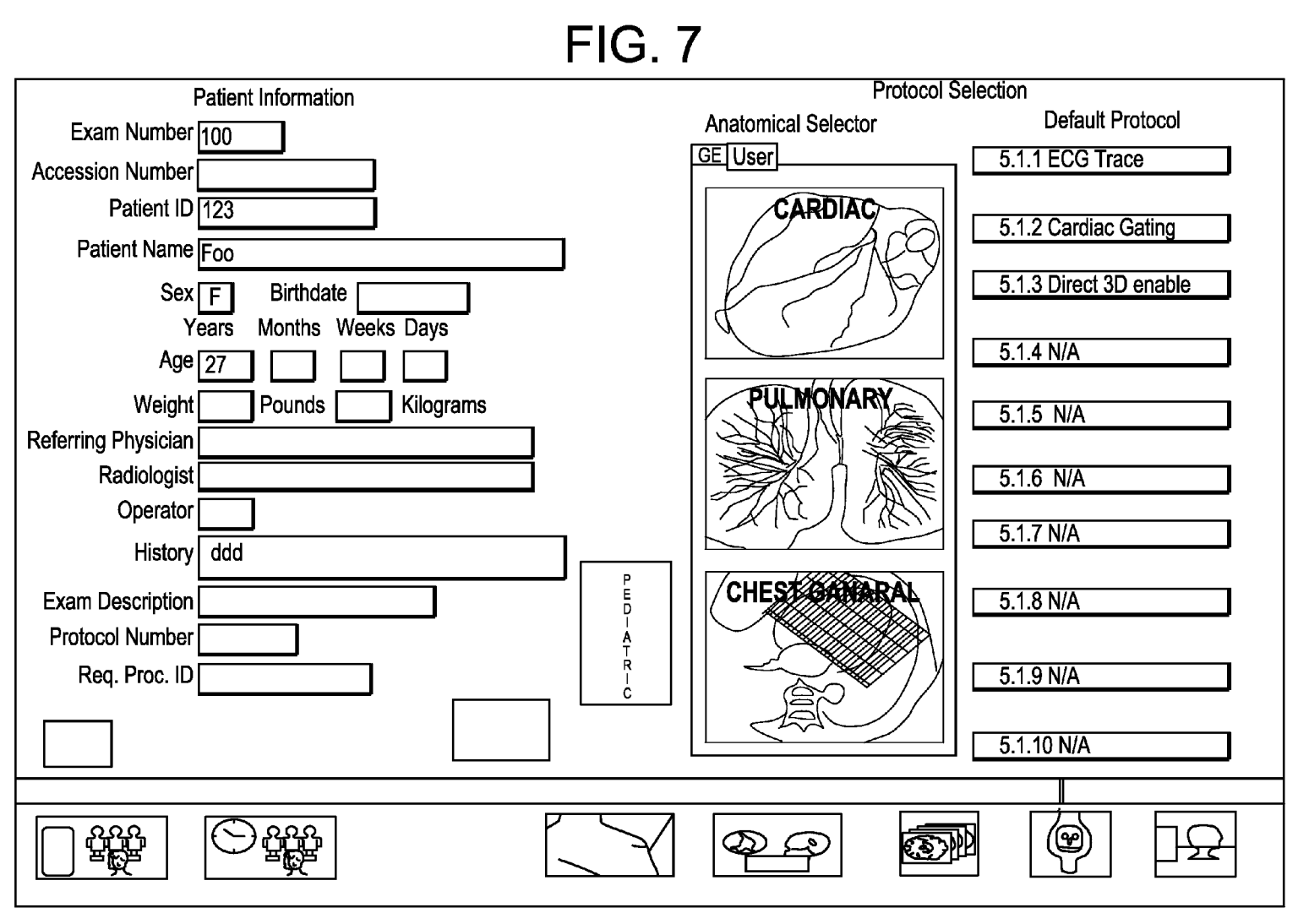
Figure 8:
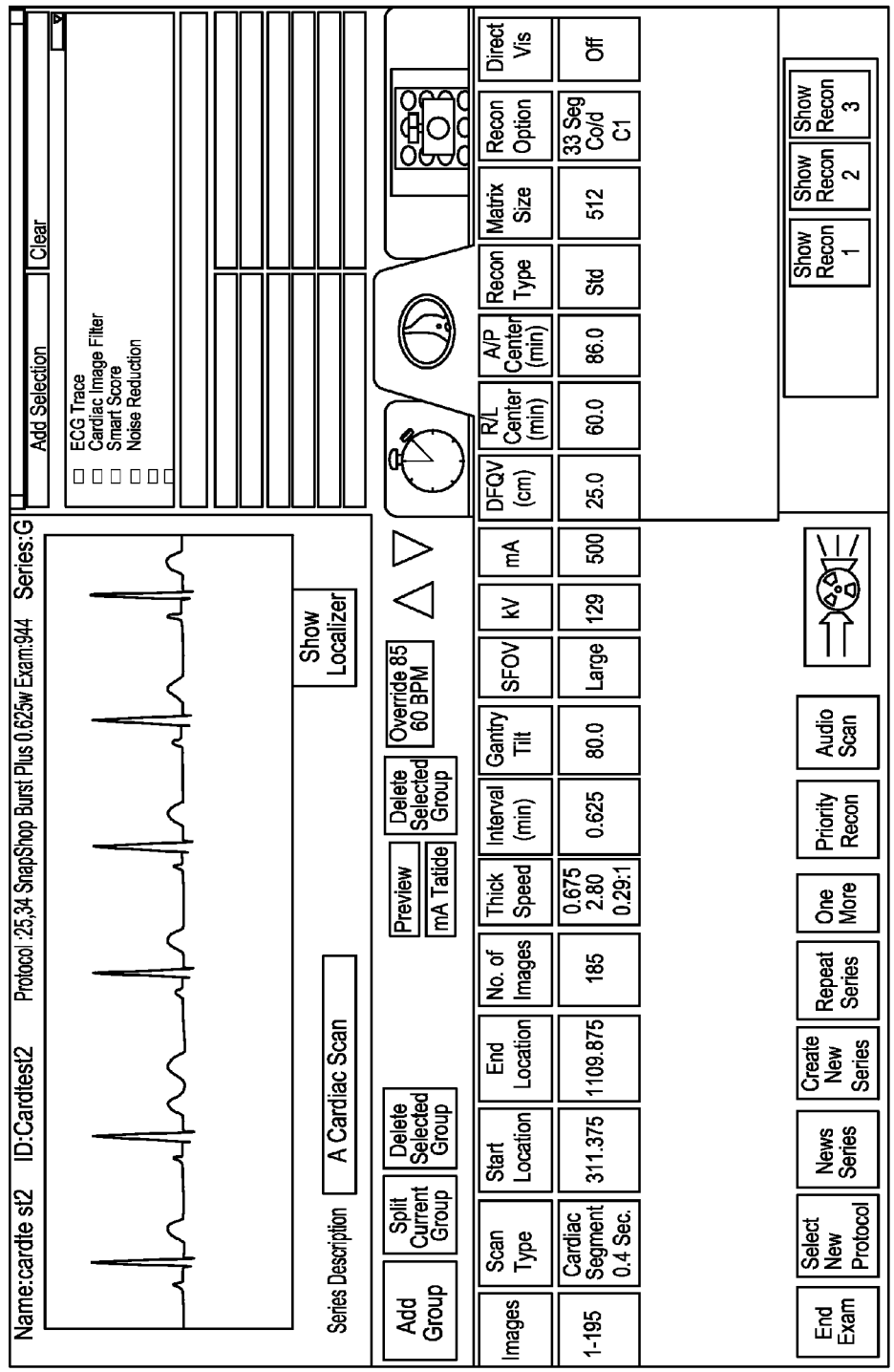
FIG. 8 illustrates, using a half-tone photograph, a user interface displayed on a display.

A description will now be given about preparing a radiographing plan. FIG. 5 shows a user work flow beginning with preparing a radiographing plan and until execution of a radiographing work. FIGS. 6, 7 and 8 show examples of picture planes used in preparing a radiographing plan. These picture planes are all graphical user interfaces displayed on the display 302.

In step 501 there are performed examination generation and input of patient information, using the picture plane shown in FIG. 6. The left half of this picture plane is a user interface for the examination generation and input of patient information. Examination number, as well as ID, sex distinction and age of patient, are inputted therein.

In step 503, an anatomical region is selected also using the picture plane of FIG. 6. The right half of this picture plane is a user interface for selecting an anatomical region.

The user interface for selecting a radiographic region is constituted by a combination of a full length diagram of the human body and plural site name boxes. The plural site boxes are, in order from above, Head, Orbit, C spine, Chest, Abdomen, Lumber, Pelvic, Lower Extremity, and General.

The selection of an anatomical region is performed by clicking a desired site name box with use of a pointing device. For example, when the site name box "Chest" is clicked, the chest is selected as an anatomical region.

When the chest is selected, the picture plane changes into the picture plane shown in FIG. 7. The right half of this picture plane is a user interface for selecting an anatomical area. The interface is constituted by an array of plural image frames. The plural image frames respectively represent plural anatomical areas belonging to the same anatomical region.

For example, the plural anatomical areas are Cardiac, Pulmonary, and Chest General, in order from above.

These are all anatomical areas or organs belonging to the chest. When an anatomical region other than the chest is selected, plural anatomical areas or organs belonging to the selected anatomical region are displayed in the same manner as above. The anatomical area as referred to herein indicates an anatomical area or organ present within the anatomical region concerned.

There are two systems of arrays of image frames which represent image areas. The two systems, which are superimposed one on the other, have respective tabs and can each be made a surface side by clicking. One of the two systems is "GE" and the other is "User." "GE" is a combination of anatomical areas provided from the manufacturer. "User" is a combination of anatomical areas constituted arbitrarily by a user.

In FIG. 7, the "User" system is a surface side. A combination of anatomical areas in the "User" system can be constituted arbitrarily by a user and therefore the user can customize it so as to be best suited for the user's own needs.

Using such a user interface, an anatomical area is selected in step 505. The selection of an anatomical area is performed by clicking a desired anatomical area with use of a pointing device. For example, when the anatomical area "Cardiac" is clicked, the heart is selected as an anatomical area.

When the heart is selected, the names of plural radiographing protocols are displayed on the plural boxes located on the right side of image frames. The boxes which display the names of radiographing protocols constitute a user interface for the selection of radiographing protocols.

The plural radiographing protocols are, for example, ECG Trace, Cardiac Gating, and Direct 3D Enable, in order from above. These are all radiographing protocols for the heart. When an anatomical area other than the heart is selected, plural radiographing protocols for the selected anatomical area are displayed in the same manner.

As to the anatomical areas in the "User" system, it is possible for a user to arbitrarily select a combination of radiographing protocols, whereby the radiographing protocols can be customized in conformity with the user's needs.

Using such a user interface, a radiographing protocol is selected in step 507. The radiographing protocol selection is performed by clicking the name of a desired radiographing protocol with use of a pointing device. For example, when "ECG Trace" is clicked, ECG Trace is selected as the radiographing protocol.

When ECG Trace is selected, the picture plane changes into such a picture plane as shown in FIG. 8. This picture plane has feature name boxes in a right upper portion. Feature names displayed in the feature name box are, for example, ECG Trace, Cardiac Image Filter, Smart Score, and Noise Reduction, in order from above. These are all features of ECG Trace. When any other radiographing protocol than ECG Trace is selected, plural features of the selected protocol are displayed in the same manner.

As to the remaining portion of the picture plane, the left side of the feature name box is a display portion of ECG (Electro Cardiogram) and the lower half of the picture plane is a user interface for operating the X-ray CT system.

Using such a user interface, the selection of a feature is performed in step 509. The selection of a feature is performed, for example, by clicking a check box of a desired feature name with use of a pointing device. For example, when the check box of the feature "ECG Trace" is clicked, ECG Trace is selected as a feature. This feature is a feature which constitutes the body of a radiographing protocol. The other features "Cardiac Image Filter," "Smart Score" and "Noise Reduction" are auxiliary features and are selected as necessary.

Thereafter, radiographing is executed in step 511. The user interface for operation located in the lower half of the picture plane is used for the execution of radiographing. Through this user interface there are set radiographing conditions such as Scan Type, Start Location, End Location, No. of Images, Thick Speed, Interval, Scan FOV (SFOV), tube voltage (kV) and tube current (mA), and thereafter Auto Scan is started.

Thus, after examination generation and input of patient information in preparing a radiographing information, there are performed selection of an anatomical region, selection of an anatomical area, selection of a radiographing protocol and selection of feature in this order. These selections are performed using respective dedicated user interfaces.

Since the user interface for the selection of an anatomical region has site name boxes related to a full length diagram of the human body, the selection of an anatomical region is easy. Likewise, since the user interface for the selection of an anatomical area has an array of plural image frames which respectively represent plural anatomical areas belonging to the same anatomical region, the selection of an anatomical area is easy.

Particularly, only the anatomical areas belonging to the same anatomical region are displayed and those belonging to the other anatomical regions are not displayed. Therefore, the selection does not require much time nor does it perplex the user. Besides, there accrues a great convenience because the anatomical areas can be customized.

Since the user interface for the selection of a radiographing protocol has plural name boxes which respectively represent plural radiographing protocols for the same anatomical area, the selection of a radiographing protocol is easy.

Particularly, only the radiographing protocols associated with the same anatomical area are displayed and those associated with the other anatomical areas are not displayed, the selection does not require much time nor does it perplex the user. Besides, there accrues a great convenience because the radiographing protocols can be customized.

Since the user interface for the selection of a feature has plural feature names of the same anatomical protocol and check boxes corresponding thereto, the selection of a feature is easy. Particularly, since only the features of the same anatomical protocol are displayed and those of the other anatomical protocols are not displayed, the selection does not require much time nor does it perplex the user.

Each feature has a configuration file. FIG. 9 shows an example of construction of the configuration file. As shown in FIG. 9, the configuration file has a matrix construction.

The columns in the matrix correspond to anatomical regions. For example, V0x corresponds to the head, V1x corresponds to the orbit, V2x corresponds to the C spine, V3x corresponds to the shoulder, V4x corresponds to the chest, V5x corresponds to the abdomen, V6x corresponds to the lumber, V7x corresponds to the pelvic, V8x corresponds to the lower extremity, and V9x corresponds to general, wherein x is 0 to 4.

The rows in the matrix correspond to anatomical areas. More particularly, Vy0 corresponds to the first area, Vy1 corresponds to the second area, Vy2 corresponds to the third area, Vy3 corresponds to the fourth area, and Vy4 corresponds to the fifth area, wherein y is 0 to 9.

The configuration file may be such that the anatomical regions correspond to the rows and the anatomical areas correspond to the columns. In this case, the number of rows is made coincident with the number of anatomical regions and the number of columns is made coincident with the number of anatomical areas.

In the configuration file, both anatomical region and area to which a feature is related are represented by flags. An example of such a display is shown in FIG. 10, which is a configuration file of the feature "ECG Trace."

In this configuration file, a flag "T" is ON in each of V40, V41, V42 and V43. Thus, it is shown that the anatomical region to which this feature is related is the chest and that the first, second, third and fourth anatomical areas are related to this feature. A flag "F" means being unrelated.

Such a configuration file is provided for each file and is stored in memory of the operating console 300. The display of features in user interfaces shown in FIG. 8 is based on such configuration files. Consequently, the management of features by the system becomes easier. Besides, since each configuration file is a matrix with columns or rows corresponding to anatomical regions and rows or columns corresponding to anatomical areas, it is easy to prepare the configuration file.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiographing planning method comprising:
selecting an anatomical region through a first user interface, the first user interface including a first selection screen for selecting the anatomical region from a plurality of anatomical regions;
selecting an anatomical area belonging to the selected anatomical region through a second user interface, the second user interface including a second selection screen for selecting the anatomical area from a plurality of anatomical areas belonging to the selected anatomical region, the second user interface displayed after selection of the anatomical region;
selecting a radiographing protocol for the selected anatomical area through a third user interface, the third user interface including a third selection screen for selecting the radiographing protocol from a plurality of radiographing protocols associated with the selected anatomical area, the third user interface displayed after selection of the anatomical area; and
selecting a feature of the selected radiographing protocol through a fourth user interface, the fourth user interface including a fourth selection screen for selecting the feature from a plurality of features associated with the selected radiographing protocol, the fourth user interface displayed after selection of the radiographing protocol, the selected feature having a configuration file including a matrix with one of columns and rows corresponding to the plurality of anatomical regions and the other of the rows and the columns corresponding to the plurality of anatomical areas.

2. A radiographing planning method according to claim 1, wherein selecting an anatomical area belonging to the selected anatomical region comprises customizing, by a user, the second user interface.

3. A radiographing planning method according to claim 1, wherein selecting a radiographing protocol for the selected anatomical area comprises customizing, by a user, the third user interface.

4. A radiographing planning method according to claim 1, wherein selecting an anatomical region through a first user interface comprises selecting at least one of a head, an orbit, a spine, a shoulder, a chest, an abdomen, a lumbar, a pelvis, a lower extremity, and a general area of a patient.

5. A radiographing planning method according to claim 1, further comprising reconstructing an image based on the selections.

6. An X-ray CT system configured to reconstruct a tomographic image based on scan data obtained by scanning a subject with X-ray, said X-ray CT system comprising:
a first user interface comprising a first selection screen for selecting an anatomical region from a plurality of anatomical regions;
a second user interface comprising a second selection screen for selecting an anatomical area from a plurality of anatomical areas belonging to the selected anatomical region, said second selection screen displayed after selection of the selected anatomical region;
a third user interface comprising a third selection screen for selecting a radiographing protocol from a plurality of radiographing protocols associated with the selected anatomical area, said third selection screen displayed after selection of the selected anatomical area; and
a fourth user interface comprising a fourth selection screen for selecting a feature from a plurality of features associated with the selected radiographing protocol, said fourth selection screen displayed after selection of the selected radiographing protocol, the selected feature having a configuration file including a matrix with one of columns and rows corresponding to the plurality of anatomical regions and the other of the rows and the columns corresponding to the plurality of anatomical areas.

7. An X-ray CT system according to claim 6, wherein said second user interface is customized by a user.

8. An X-ray CT system according to claim 6, wherein said third user interface is customized by a user.

9. An X-ray CT system according to claim 6, wherein said first selection screen is configured to display the plurality of anatomical regions, the plurality of anatomical regions including at least one of a head, an orbit, a spine, a shoulder, a chest, an abdomen, a lumbar, a pelvis, a lower extremity, and a general area of a patient.

10. An X-ray CT system according to claim 6, further comprising an operator console configured to reconstruct the tomographic image based on the selections.

11. A radiography plan assisting device comprising:
a first user interface for selecting an anatomical region, said first user interface comprising a first selection screen configured to display a plurality of anatomical regions including the selected anatomical region;
a second user interface for selecting an anatomical area associated with the selected anatomical region, said second user interface comprising a second selection screen configured to display a plurality of anatomical areas associated with the selected anatomical region and including the selected anatomical area, said second user interface displayed after the selection of the selected anatomical region;
a third user interface for selecting a radiographing protocol associated with the selected anatomical area, said third user interface comprising a third selection screen configured to display a plurality of radiographing protocols associated with the selected anatomical area and including the selected radiographing protocol, said third user interface displayed after the selection of the selected anatomical area; and
a fourth user interface for selecting a feature associated with the selected radiographing protocol, said fourth user interface comprising a fourth selection screen configured to display a plurality of features associated with the selected radiographing protocol and including the selected feature, said fourth user interface displayed after the selection of the selected radiographing protocol, the selected feature associated with the selected radio radiographing protocol having a configuration file including a matrix with one of columns and rows corresponding to the plurality of anatomical regions and the other of the rows and the columns corresponding to the plurality of anatomical areas.

12. A radiography plan assisting device according to claim 11, wherein said second user interface comprises a customizable user interface for selecting an anatomical area associated with the selected anatomical region.

13. A radiography plan assisting device according to claim 11, wherein said third user interface comprises a customizable user interface for selecting a radiographing protocol associated with the selected anatomical area.

14. A radiography plan assisting device according to claim 11, wherein said first selection screen is configured to display the plurality of anatomical regions, the plurality of anatomical regions including at least one of a head, an orbit, a spine, a shoulder, a chest, an abdomen, a lumbar, a pelvis, a lower extremity, and a general area of a patient.

* * * * *